United States Patent [19]

Brooks et al.

[11] Patent Number: 5,068,251
[45] Date of Patent: Nov. 26, 1991

[54] LIPOXYGENASE INHIBITING COMPOUNDS

[75] Inventors: Dee W. Brooks, Libertyville; Karen E. Rodriques, Grayslake, both of Ill.

[73] Assignee: Abbott Laboratories, Abbott Park, Ill.

[21] Appl. No.: 285,439

[22] Filed: Dec. 16, 1988

[51] Int. Cl.$^5$ .................... C07C 275/68; A61K 31/17
[52] U.S. Cl. .................................... 514/506; 514/575; 560/314; 562/623
[58] Field of Search ............... 514/568, 594, 596, 588, 514/506, 575; 564/56, 44; 560/110, 100, 314; 562/623

[56]      References Cited
U.S. PATENT DOCUMENTS

| | | | |
|---|---|---|---|
| 2,999,110 | 9/1961 | Lott et al. | 562/623 |
| 3,895,023 | 7/1975 | Sharpe | 560/30 |
| 4,393,075 | 7/1983 | Terao et al. | 514/519 |
| 4,608,390 | 8/1986 | Summers, Jr. | 562/623 |
| 4,623,661 | 11/1986 | Summers, Jr. | 562/622 |
| 4,695,586 | 9/1987 | Varma et al. | 514/469 |
| 4,769,387 | 9/1988 | Summers et al. | 514/314 |
| 4,943,587 | 7/1990 | Cetenko et al. | 548/495 |

FOREIGN PATENT DOCUMENTS 0039051  11/1981  European Pat. Off. .

OTHER PUBLICATIONS

Corey JACS 1984 106 1503–1504.
Wojnar, et al Chemical Abstracts vol. 90, 1979, Abstract 132797h.
Fujimura et al DE 3012190 Mar. 1979 Chemical Abstracts vol. 94, 1981 Abstract No. 52955a.

Primary Examiner—Mukund J. Shah
Assistant Examiner—E. C. Ward
Attorney, Agent, or Firm—Jerry F. Janssen; Steven F. Weinstock

[57]      ABSTRACT

Compounds of the formula:

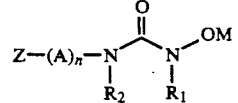

wherein A is $CH_2$; n is 0 or 1; $R_1$ and $R_2$ are independently selected from the group consisting of hydrogen, alkyl, alkenyl, aralkyl and cycloalkyl; Z is the residue from a non-steroidal anti-inflammatory carboxylic acid compound; and M is a pharmaceutically acceptable cation or a metabolically cleavable group; and the pharmaceutically acceptable salts thereof; and a non toxic pharmaceutically acceptable carrier.

These compounds are useful as inhibitors of 5-lipoxygenase.

5 Claims, No Drawings

LIPOXYGENASE INHIBITING COMPOUNDS

BACKGROUND OF THE INVENTION

This invention relates to compounds which inhibit lipoxygenase enzymes. It also relates to methods of inhibiting lipoxygenase enzymes in human and animal hosts in need of such treatment.

The lipoxygenases are a family of enzymes which catalyze the oxygenation of arachidonic acid. The enzyme 5-lipoxygenase converts arachidonic acid to 5-hydroperoxy-eicosatetraenoic acid (5-HPETE). This is the first step in the metabolic pathway yielding 5-hydroxyeicosatetraenoic acid (5-HETE) and the important class of potent biological mediators, the leukotrienes (LTs). Similarly 12- and 15-lipoxygenase convert arachidonic acid to 12- and 15-HPETE respectively. Biochemical reduction of 12-HPETE leads to 12-HETE, while 15-HPETE is the precursor of the class of biological agents known as the lipoxins. 12-HETE has been found in high levels in epidermal tissue of patients with psoriasis. Lipoxins have recently been shown to stimulate elastase and superoxide ion release from neutrophils.

A variety of biological effects are associated with these products from lipoxygenase metabolism of arachidonic acid and they have been implicated as mediators in various disease states. For example, the LTs $C_4$ and $D_4$ are potent constrictors of human airways in vitro and aerosol administration of these substances to non-asthmatic volunteers induces bronchoconstriction. $LTB_4$ and 5-HETE are potent chemotactic factors for inflammatory cells such as polymorphonuclear leukocytes. They also have been found in the synovial fluid of rheumatoid arthritic patients. Leukotrienes have been implicated as important mediators in allergic rhinitis, psoriasis, adult respiratory distress syndrome, inflammatory bowel disease, endotoxin shock, and ischemia induced myocardial injury. The biological activity of the LTs has been reviewed by Lewis and Austen, J. Clinical Invest. 73, 89, 1984 and by J. Sirois, Adv. Lipid Res., 21, 78, (1985).

Thus, lipoxygenase enzymes are believed to play an important role in the biosynthesis of mediators of asthma, allergy, arthritis, psoriasis, and inflammation. Agents which block or modulate the activity of lipoxygenase enzymes will likely be useful in the treatment of diseases involving leukotriene pathogenesis. Some examples of 5-lipoxygenase inhibitors known to the art are: AA-861, disclosed in U.S. Pat. No. 4,393,075, issued July 12, 1983, to Terro et al.; pyrazolopyridines, disclosed in European Patent Application of Iriburn et al., S. N. 121,806, published Oct. 17, 1984; arachidonyl hydroxamic acid, disclosed in E. J. Corey et al., J. Am. Chem. Soc., 106, 1503 (1984) and European Patent Application of P. H. Nelson, S. N. 104,468, published Apr. 4, 1984; BW-755C, disclosed in Radmark et al., FEBS Lett, 110, 213,(1980); nordihydroguaiaretic acid, disclosed in Marris et al., Prostaglandins, 19, 371 (1980); Rev-5901, disclosed in Coutts, Meeting Abstract 70, Prostaglandins and Leukotrienes 7384; benzoxaprofen, disclosed in J. Walker, Pharm. Pharmacol., 31, 778 (1979); and hydroxamic acids, disclosed in U.S. Pat. Nos. 4,608,390 and 4,623,661, issued Aug. 16, and Nov. 18, 1986 respectively.

SUMMARY OF THE INVENTION

The compounds of this invention possess unexpected activity as inhibitors of lipoxygenase enzymes, and reduce the biosynthesis of leukotrienes $B_4$, $C_4$, $D_4$ and $E_4$. The compounds and pharmaceutical compositions containing these compounds are useful for the treatment of disease states in mammals, which involve leukotrienes $B_4$, $C_4$, $D_4$ and $E_4$.

The compounds of this invention are of the formula:

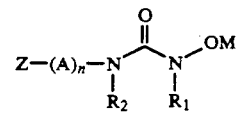

I wherein A is $CH_2$; n is 0 or 1; $R_1$ and $R_2$ are independently selected from the group consisting of hydrogen, alkyl, alkenyl, aralkyl and cycloalkyl; Z is the residue from a non-steroidal anti-inflammatory carboxylic acid compound; and M is a pharmaceutically acceptable cation or a metabolically cleavable group; and the pharmaceutically acceptable salts thereof.

This invention also relates to pharmaceutical compositions containing a compound of formula I and a pharmaceutically acceptable carrier and a method of inhibiting lipoxygenase enzymes comprising the administration to a host in need of such treatment of a compound of formula I.

DETAILED DESCRIPTION OF THE INVENTION

The present invention provides for compounds which exhibit unexpected activity for lipoxygenase enzyme inhibition, particularly, 5-lipoxygenase, and thereby reduce the biosynthesis of leukotrienes $B_4$, $C_4$, $D_4$ and $E_4$.

The novel compounds of this invention are those of the formula:

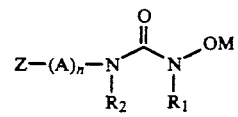

I wherein A is $CH_2$; n is 0 or 1; $R_1$ and $R_2$ are independently selected from the group consisting of hydrogen, alkyl, alkenyl, aralkyl and cycloalkyl; Z is the residue from a non-steroidal anti-inflammatory carboxylic acid compound; and M is a pharmaceutically acceptable cation or a metabolically cleavable group; and the pharmaceutically acceptable salts thereof.

When $R_1$ or $R_2$ are other than hydrogen, they may be optionally substituted by alkoxy, halo, cyano, amino, carboxy, COX, OCOX or NHCOX radicals where X is alkyl, alkoxy, amino, alkylamino, dialkylamino or aryl.

The term "alkyl" as used herein refers to straight and branched chain radicals having 1 to 12 carbon atoms which may be optionally substituted as defined above. Representative of such radicals are methyl, ethyl, n-propyl, isopropyl, n-butyl, sec-butyl, isobutyl, tert-butyl, and the like.

The term "alkenyl" as used herein refers to straight and branched chain unsaturated radicals having 2 to 12 carbon atoms, which may be optionally substituted as defined above. Representative of such groups are ethenyl, 1-propenyl, 2-propenyl, 2-methyl-1-propenyl, 1-butenyl, 2-butenyl, and the like.

The term "aralkyl" as used herein refers to a substituted or unsubstituted aromatic ring group attached to an alkyl radical as defined above, including, but not limited to benzyl, alpha- or beta-naphthylmethyl, halobenzyl, nitrobenzyl, alkoxybenzyl, and the like.

The term "cycloalkyl" as used herein refers to cyclic or bicyclic radicals having 3 to 12 carbon atoms which may be optionally substituted as defined above. Representative of such groups are cyclopropyl, cyclobutyl, cyclopentyl, cyclohexyl, norbornyl, 2-chlorocyclohexyl, and the like.

The term "aryl" as used herein refers to mono or polycyclic hydrocarbon groups containing fused or nonfused aromatic ring systems which may contain one or more hetero atoms such as O, N or S in the ring system and which may be optionally substituted as defined herein. Representative of such groups are phenyl, naphthyl, biphenyl, triphenyl, pyridinyl, pyrrolyl, pyrimidinyl, furyl, thienyl, indolyl, pyrazinyl, isoquinolyl, benzopyranyl, benzofuryl, benzothiophinyl, imidazolyl, carbazolyl, and the like.

The term "alkoxy" as used herein refers to straight and branched chain oxygen ether radicals having 1 to 12 carbon atoms which may be optionally substituted. Representative of such groups are methoxy, ethoxy, isopropoxy, n-butoxy, sec-butoxy, isobutoxy, tert-butoxy, and the like.

The terms "halo" and "halogen" as used herein refer to radicals derived from the elements fluorine, chlorine, bromine and iodine.

The term "halo-substituted" alkyl, alkenyl or alkinyl refers to a radical as described above substituted with one or more halogens, and which may also be additionally substituted a defined above. Representatives of such groups are chloromethyl, trifluoromethyl, 2,2,2-trichloroethyl, 2,2-dichloro-1-hydroxybutyl, and the like.

The term "pharmaceutically acceptable cation" as used herein refers to hydrogen and the nontoxic cations based on the alkali and alkaline earth metals, such as sodium, lithium, potassium, calcium, magnesium, and the like, as well as those based on nontoxic ammonium, quarternary ammonium and amine cations, including, but not limited to, ammonium, tetramethylammonium, tetraethylammonium, methylamino, dimethylamino, trimethylamino, triethylamino, and ethylamino cations, and the like.

The term "metabolically cleavable group" refers to groups which can be cleaved from the molecule by metabolic processes and be substituted with hydrogen or a salt, or form a group which yields an active enzyme inhibitor when the cleavable group is removed from the molecule. Examples of metabolically cleavable groups include COR, COOR, CONRR and CH$_2$OR groups where R is selected independently from alkyl, aryl or substituted aryl. Representative metabolically cleavable groups include acetyl, methoxycarbonyl, benzoyl, tetrahydropipanyl, methoxymethyl and trimethylsilyl groups.

The term "residue" as used herein with respect to a non-steroidal anti-infammatory carboxylic acid compound is intended to represent that portion of the anti-inflammatory compound which remains after removal of the —COOH portion of the molecule.

The chemical structure of the non-steroidal anti-inflammatory drugs whose residues are encompassed by formula I is not critical provided the drugs contain a carboxylic acid function. Suitable anti-inflammatory agents include, but are not limited to, the following:

(1) benoxaprofen
(2) benzofenac
(3) bucloxic acid
(4) butibufen
(5) carprofen
(6) cicloprofen
(7) cinmetacin
(8) clidanac
(9) clopirac
(10) diclofenac
(11) etodolac
(12) fenbufen
(13) fenclofenac
(14) fenclorac
(15) fenoprofen
(16) fentiazac
(17) flunoxaprofen
(18) furaprofen
(19) furobufen
(20) furofenac
(21) ibuprofen
(22) indomethacin
(23) indoprofen
(24) isoxepac
(25) ketoprofen
(26) lonazolac
(27) metiazinic
(28) miroprofen
(29) naproxen
(30) oxaprozin
(31) oxepinac
(32) pirprofen
(33) pirazolac
(34) protizinic acid
(35) sulindac
(36) suprofen
(37) tiaprofenic acid
(38) tolmetin
(39) zomepirac.

The term "pharmaceutically acceptable salts" refers to the relatively non-toxic, inorganic or organic acid addition salts and alkaline earth metal salts of the compounds of this invention. These salts can be prepared in situ during the final isolation and purification of the compounds, or by separately reacting the free base with a suitable organic or inorganic acid. Representative salts include the hydrochloride, hydrobromide, sulfate, phosphate, nitrate, bisulfate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactobionate, lauryl sulphate, and the like. Representative alkali or alkaline earth metal sales include sodium, calcium, potassium and magnesium salts, and the like. It will be apparent to those skilled in the art that, depending upon the number of available amino groups for salt formation, the salts of this invention can be per-N-salts.

Certain compounds of this invention may exist in optically active forms. The R and S isomers and mixtures thereof, including racemic mixtures as well as the cis and trans mixtures are contemplated by this invention. Additional asymmetric carbon atoms may be present in a substituent group such as an alkyl group. All such isomers as well as the mixtures thereof are intended to be included in the invention.

The present invention includes one or more of the compounds of Formula I formulated into compositions together with one or more non-toxic pharmaceutically acceptable carriers, adjuvants or vehicles which are collectively referred to herein as carriers, for parenteral injection, for oral administration in solid or liquid form, for rectal administration, and the like.

The compositions can be administered to humans and animals either orally, rectally, parenterally (intravenously, intramuscularly or subcutaneously), intracisternally, intravaginally, intraperitoneally, locally (powders, ointments or drops), or as a buccal or nasal spray.

Compositions suitable for parenteral injection may comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, as for example, parabens, chlorobutanol, phenol, sorbic acid, and the like. It may also be desirable to include isotonic agents, as for example, sugars, sodium chloride and the like. Prolonged absorption of the injectable pharmaceutical form can be brought about by the use of agents delaying absorption, for example, aluminum monosterate and gelatin.

If desired, and for more effective distribution, the compounds can be incorporated into slow release or targeted delivery systems such as polymer matrices, liposomes, and microspheres. They may be sterilized, for example, by filtration through a bacteria-retaining filter, or by incorporating sterilizing agents in the form of sterile solid compositions which can be dissolved in sterile water, or some other sterile injectable medium immediately before use.

Solid dosage forms for oral administration include capsules, tablets, pills, powders and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules using such excipients as lactose or milk sugar as well as high molecular weight polyethylene glycols, and the like.

Solid dosage forms such as tablets, dragees, capsules, pills and granules can be prepared with coatings and shells, such as enteric coatings and others well known in this art. They may contain opacifying agents, and can also be of such composition that they release the active compound or compounds in a certain part of the intestinal tract in a delayed manner. Examples of embedding compositions which can be used are polymeric substances and waxes.

The active compounds can also be in micro-encapsulated form, if appropriate, with one or more of the abovementioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, tetrahydrofurfuryl alcohol, polyethylene glycols and fatty acid esters of sorbitan or mixtures of these substances, and the like.

Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of this invention with suitable non-irritating excipients or carriers such as cocoa butter, polyethylene glycol or a suppository wax, which are solid at ordinary temperatures but liquid at body temperature and therefore, melt in the rectum or vaginal cavity and release the active component.

Dosage forms for topical administration of a compound of this invention include powders, sprays and inhalants. The active component is admixed under sterile conditions with a pharmaceutically acceptable carrier and any needed preservatives, buffers or propellants as may be required. Opthalmic formulations, eye ointments, powders and solutions are also contemplated as being within the scope of this invention.

Actual dosage levels of active ingredient in the compositions of the invention may be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors.

Total daily dose of the compounds of this invention administered to a host in single or divided doses may be in amounts, for example, of from about 0.001 to about 100 mg/kg body weight/day and preferably 0.01 to 10 mg/kg body weight/day. Unit dose compositions may contain such amounts as may be used to make up the total daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

SYNTHESIS OF THE COMPOUNDS OF THIS INVENTION

Compounds of this invention can be prepared by the following processes. In certain cases where the nonsteroidal anti-inflammatory compound contains functional groups which might interfere with the desired transformation outlined in the following processes, it is recognized that common methods of protection of these groups followed by deprotection at a later stage in the preparation of the desired product can be applied. A general reference source for methods of protection and deprotection is T. W. Greene, "Protective Groups in Organic Synthesis", Wiley-Interscience, N.Y., 1981.

Process 1 involves reaction of a carboxylic acid of the general formula, Z—COOH, where Z is a group as previously defined, with diphenylphosphoryl azide (DPPA) in the presence of triethylamine to form the intermediate isocyanate, Z—N=C=O. The isocyanate is subsequently reacted with a hydroxylamine, $NHR_1OM$, where $R_1$ and M are groups as previously defined, to provide the desired hydroxyurea compound, Z—NH—CO—N(OM)$R_1$.

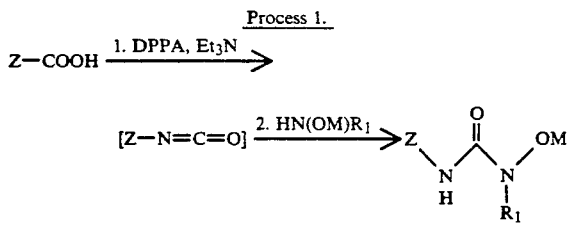

Process 1.

The use of DPPA for the conversion of a carboxylic acid into an isocyanate is a known procedure, see K. Ninamiya et. al., Tetrahedron, 1974, 30, 2151. Alternative known methods for the conversion of a carboxylic acid to the corresponding isocyanate can also be employed in the first part of Process 1 such as treatment of the carboxylic acid, Z—COOH with thionyl chloride or oxalyl chloride to provide the corresponding acid chloride, Z—COCl which is then reacted with an azide salt to form the acylazide intermediate, Z—CON$_3$ which upon heating fragments to provide the isocyanate, Z—N=C=O.

The following preferred embodiments are for the purpose of illustrating the use of Process 1 to prepare representative compounds of this invention and do not limit of the specification and claims in any way whatsoever.

EXAMPLE 1

N'-hydroxy-N'-methyl-N-(4'-chlorobenzoyl-5-methoxy-2-methyl-3-indolyl)methyl urea To a stirred solution of indomethacin (2.0 g, 5.6 mmol) in benzene (30 mL) was added triethylamine (0.57 g, 5.6 mmol) followed by diphenylphosphoryl azide (1.54 g, 5.6 mmol). After heating the mixture at 90° C. for one hour, a solution of N-methylhydroxylamine hydrochloride salt (0.94 g, 11.2 mmol) and triethylamine (1.13 g, 11.2 mmol) in water (1 mL) was added and the reaction was heated at 90° C. for 18 hours. The reaction was then poured into aqueous saturated NH$_4$Cl (30 mL) and extracted with ethylacetate (3×30 mL). The combined organic extract was dried over MgSO$_4$ and concentrated. The resulting residue was purified by chromatography (silica gel, ether-hexanes, 9:1) followed by crystallization from ethylacetate-hexane to provide the desired product (320 mg).

mp=178°-79° C.; NMR (300MHz, DMSO-d6) 2.30 (3H, s), 2.95 (3H, s), 3.76 (3H, s), 4.31 (2H, d, J =6 Hz), 6.70 (1H, dd, J=3 Hz), 6.92 (1H, d, J=9 Hz), 7.37 (2H, m), 7.66 (4H, m), 9.33 (1H, s).

MS: M+ =402

Analysis Calc'd for C$_{20}$H$_{20}$N$_3$O$_4$Cl : C, 59.78; H, 5.02; N, 10.46. Found: C, 59.65; H, 5.08; N, 10.32

EXAMPLE 2

N'-hydroxy-N-[1-(6-methoxynaphthalen-2yl)ethyl]urea

To a stirred solution of naproxen (2.0 g, 8.7 mmol) in benzene (45 mL) was added triethylamine (0.88 g, 8.7 mmol) followed by diphenylphosphoryl azide (2.39 g, 8.7 mmol) and the mixture was heated at 90° C. for one hour. Then, O- trimethylsilylhydroxylamine (1.83 g, 17.4 mmol) was added and the mixture was heated at 90° C. for 4 hours. The reaction was then poured into aqueous saturated NH$_4$Cl (30 mL) and extracted with ethylacetate (3×50 mL). The combined organic extract was dried over MgSO$_4$ and concentrated. The resulting residue was purified by crystallization from ethylacetate-hexane to provide the desired product (911 mg).

mp=174.5°-175.5° C.; NMR (300 MHz, DMSO-d6) 1.47 (3H, d, J=b 7.5 Hz), 3.86 (3H, s), 4.97 (1H, m), 7.02 (1H, d, J=9 Hz), 7.14 (1H, dd, J=2.5 Hz), 7.28 (1H, d, J=3 Hz), 7.50 (1H, dd, J=1.5 Hz), 7.72 (1H, bs), 7.75 (1H, s), 7.78 (1H, s), 8.37 (1H, d, J=0.5 Hz), 8.64 (1H, d, J=1 Hz).

MS: M+ =261

Analysis Calc'd for C$_{14}$H$_{16}$N$_2$O$_3$: C, 64,60; H, 6.20; N, 10.76. Found: C, 64.17; H, 6.36; N, 10.57

EXAMPLE 3

N'-hydroxy-N-[1-(4-(2'methylpropyl)phenyl)ethyl]urea

The same method as described for Example 2 was used substituting ibuprofen instead of naproxen to provide the desired product. (304 mg)

mp.=131.5°-132° C.; NMR (300MHz, DMSO-d6) 0.85 (6H, d, J=7 Hz), 1.37 (3H, d, J=7.5 Hz), 1.80 (1H, septet), 2.41 (2H, d, J=7.5 Hz), 4.81 (1H, m), 6.89 (1H, m), 7.08 (2H, m), 7.24 (2H, m), 8.34 (IH, d, J=1 Hz), 8.61 (1H, d, J=1.5 Hz).

MS: M+ =237

Analysis Calc'd for C$_{13}$H$_{20}$N$_2$O$_2$: C, 66.07 ; H, 8.53; N, 11.86. Found: C, 65.83; H, 8.43; N, 11.74

Process 2 involves the reaction of a carboxylic acid of the general formula, Z—COOH, where Z is a group as previously defined, with thionyl chloride or oxalyl chloride to provide the corresponding acid chloride, Z—COCl which is then reacted with ammonium hydroxide or an amine, NHR$_2$ to provide the corresponding amide Z—CONHR$_2$ which is subsequently subjected to reduction with reducing agents such as diborane or lithium aluminum hydride to provide the methylene homologated amine Z—CH$_2$—NHR$_2$. This amine or its acid addition salts are treated with phosgene or a phosgene equivalent to form the intermediate isocyanate which is not isolated but directly reacted with a hydroxylamine, NHR$_1$OM, where R$_1$ and M are groups as previously defined, to provide the desired hydroxyurea compound, Z—CH$_2$—NR$_2$—CO—N(OM)R$_1$.

Process 2.

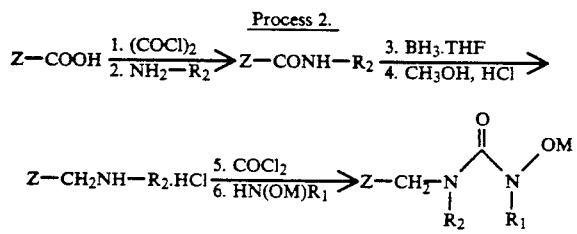

The following preferred embodiments illustrate the use of Process 2 to prepare representative compounds of this invention and do not limit the specification and claims in any way whatsoever.

EXAMPLE 4

N'-hydroxy-N-[2-(4-(2'-methylpropyl)phenyl)]urea

To a stirred solution of ibuprofen (2.58 g, 12.5 mmol) in dichloromethane (60 mL) was added dropwise oxalyl chloride (1.75 g, 13.75 mmol). The mixture was stirred for 4 hours. and then concentrate in vacuo. The resulting residue was dissolved in a minimum amount of tetrahydrofuran and then added to a stirred solution of 10% NH$_4$OH (60 mL). After stirring for one hour the mixture was extracted with ethylacetate (3×60 mL) and the combined organic extract was dried over MgSO$_4$ and concentrated to provide the corresponding amide intermediate, 4-(2'-methylpropyl)phenylacetamide.

To a stirred solution of the amide, from the previous step, in tetrahydrofuran (THF)(50 mL) was added dropwise a solution of BH$_3$.THF (25.0 mL of 1.0M in THF, 25.0 mmol). After the addition the mixture was refluxed for 1.5 hours, then cooled and saturated methanolic HCl (10 mL) was added dropwise with caution. The mixture was refluxed for 1 hour and then concentrated in vacuo to afford the amine salt, 2-[4-(2'-methylpropyl)phenyl]-1-propylamine hydrochloride.

To a stirred suspension of the amine hydrochloride, directly from the previous step, in toluene (10 mL) at 100° C. was added dropwise a solution of phosgene (63 mL, 20% in toluene, 125 mmol). The mixture was heated for 30 minutes and then toluene was distilled leaving a volume of 5 mL. A solution of hydroxylamine hydrochloride (1.06 g, 15.25 mmol) and triethylamine (1.92 g, 19.0 mmol) in a mixture of water (1.5 mL) and THF (25 mL) was added dropwise at room temperature. After stirring for 30 minutes, the mixture was poured into 1N HCl (50 mL) and extracted with ethylacetate (3×50 mL). The combined organic extract was dried over MgSO$_4$ and concentrated. The resulting residue was purified by chromatography (silica gel, ether-hexanes, 9:1) followed by crystallization from ethylacetate-hexanes to provide the desired product (316 mg).

mp.=84°-85° C.; NMR (300 MHz, DMSO-d6) 0.86 (6H, d, J=7 Hz), 1.14 (2H, d, J=7 Hz), 1.80 (1H, m), 2.40 (2H, d, J=7.5 Hz), 2.88 (1H, q, J=7 Hz), 3.19 (2H, dd, J=7 Hz), 6.50 (1H, t, J=6 Hz), 7.10 (4H, m), 8.27 (1H, s), 8.53 (1H, s).

MS: M+ =251

Analysis Calc'd for C$_{14}$H$_{22}$N$_2$O$_2$ : C, 67.16; H, 8.86; N, 11.19. Found: C, 67.25; H, 8.82; N, 11.17

INHIBITION OF 5-LIPOXYGENASE

Inhibition of 5-lipoxygenase activity was determined using the 20,000×g supernatant from homogenized RBL-1 cells in a similar manner as that described by Dyer and coworkers (Dyer, R. D.; Haviv, F.; Hanel, A. M.; Bornemier, D. A.; Carter, G. W. Fed. Proc , Fed. Am. Soc. Exp. Biol. 1984, 43, 1462A). Inhibitory potencies for representative examples of this invention are listed in Table 1. IC$_{50}$ values (concentration of compound producing 50% enzyme inhibition) were calculated by linear regression analysis of percentage inhibition versus log inhibitor concentration plots.

TABLE I

| In vitro 5-lipoxygenase inhibitory potency of representative compounds of this invention. | |
|---|---|
| Example | IC$_{50}$ (10$^{-6}$M) |
| 1 | 0.2 |
| 2 | 4.8 |
| 3 | 2.9 |
| 4 | 1.9 |

INHIBITION OF LEUKOTRIENE BIOSYNTHESIS

Inhibition of the biosynthesis of leukotrienes in vivo after intraperitoneal administration of compound was determined using a rat peritoneal anaphylaxis model. In this model rats were injected intraperitoneally (ip) with rabbit antibody to bovine serum albumin (BSA) and three hours later injected ip with BSA to induce an antgen-antibody response. Rats were sacrificed 15 minutes after this challenge and the peritoneal fluids were collected and analyzed for leukotriene levels. Test compound was injected intraperitoneal 30 minutes prior to the antigen challenge. Percent inhibition values were determined by comparing the treatment group to the mean of the control group. From the results of this assay it is demonstrated that compounds of this invention are orally effective in preventing the in vivo biosynthesis of leukotrienes. The compound of Example 1 gave 81% inhibition of leukotriene biosynthesis in vivo at 40 mg/kg i.p.dose.

We claim:

1. A compound of the formula

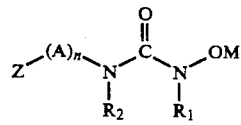

wherein A is —CH$_2$—; n is 0 or 1; R$_1$ and R$_2$ are independently selected from the group consisting of hydrogen, alkyl alkenyl, aralkyl and cycloalkyl; Z is the residue from a non-steroidal anti-inflammatory carboxylic acid compound selected from ibuprofen and naproxen;

and M is a pharmaceutically acceptable cation or a metabolically cleavable group; or a pharmaceutically acceptable salt thereof.

2. A compound as in claim 1 which is selected from the group consisting of N'-hydroxy-N-[1-(6-methoxynaphthalen-2-yl)ethyl]urea, N'-hydroxy-N-[1-(4-(2'-methylpropyl)phenyl)ethyl]urea and N'-hydroxy-N-[2-(4-(2'-methylpropyl)phenyl)]-1-propyl urea.

3. A pharmaceutical composition comprising a therapeutically effective amount of a compound of the formula

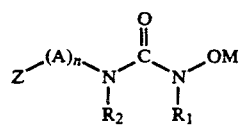

wherein A is —$CH_2$—; n is 0 or 1; $R_1$ and $R_2$ are independently selected from the group consisting of hydrogen, alkyl alkenyl, aralkyl and cycloalkyl; Z is the residue from a non-steroidal anti-inflammatory carboxylic acid compound selected from ibuprofen and naproxen; and M is a pharmaceutically acceptable cation or a metabolically cleavable group; or a pharmaceutically acceptable salt thereof.

4. A method for the inhibition of lipoxygenase enzymes comprising administering to a mammal in need of such treatment an effective amount of a compound of the formula

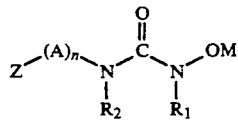

wherein A is —$CH_2$—; n is 0 or 1; $R_1$ and $R_2$ are independently selected from the group consisting of hydrogen, alkyl alkenyl, aralkyl and cycloalkyl; Z is the residue from a non-steroidal anti-inflammatory carboxylic acid compound selected from ibuprofen and naproxen; and M is a pharmaceutically acceptable cation or a metabolically cleavable group; or a pharmaceutically acceptable salt thereof; and a non-toxic pharmaceutically acceptable carrier.

5. A method for treating asthma, allergy, arthritis, psoriasis and inflammation comprising administering to a mammal in need of such treatment an effective amount of a compound of the formula

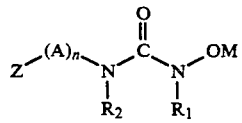

wherein A is —$CH_2$—; n is 0 or 1; $R_1$ and $R_2$ are independently selected from the group consisting of hydrogen, alkyl alkenyl, aralkyl and cycloalkyl; Z is the residue from a non-steroidal anti-inflammatory carboxylic acid compound selected from ibuprofen and naproxen; and M is a pharmaceutically acceptable cation or a metabolically cleavable group or a pharmaceutically acceptable salt thereof; and a non-toxic pharmaceutically acceptable carrier.

* * * * *

UNITED STATES PATENT AND TRADEMARK OFFICE
CERTIFICATE OF CORRECTION

PATENT NO. : 5,068,251
DATED : November 26, 1991
INVENTOR(S) : Dee W. Brooks; Karen E. Rodriques It is certified that error appears in the above-identified patent and that said Letters Patent is hereby corrected as shown below:

Column 8, Line 21: Replace "mp=178°-79°C" with --mp=178°-179°C--

Column 8, Line 44: Replace "1.47(3H, d, J=b 7.5Hz)" with
--1.47(3H, d, J=7.5 Hz)--.

Column 10, Line 43: Replace "antgen-antibody" with --antigen-antibody--.

Signed and Sealed this

First Day of June, 1993

Attest:

MICHAEL K. KIRK

*Attesting Officer*         *Acting Commissioner of Patents and Trademarks*